United States Patent [19]

Egraz et al.

[11] Patent Number: 5,973,203
[45] Date of Patent: Oct. 26, 1999

[54] PROCESS FOR PREPARATION OF ACRYLIC OR METHACRYLIC ACID AMIDES

[75] Inventors: Jean-Bernard Egraz, Ecully; Jean-Marc Suau, Lucenay; Maryvonne Brigodiot-Ignazi, Malabry; Isabelle Peixoto, Paris; Thierry Lalot, Viry-Chatillon, all of France

[73] Assignee: Coatex S.A., Genay, France

[21] Appl. No.: 08/991,002

[22] Filed: Dec. 15, 1997

[30] Foreign Application Priority Data

Dec. 13, 1996 [FR] France ................................. 9615612

[51] Int. Cl.⁶ ...................... C07C 231/02; C12P 13/00
[52] U.S. Cl. .................. 564/135; 435/128; 435/129; 435/197; 435/876; 435/939; 564/204; 564/206
[58] Field of Search .................. 564/135, 204, 564/206; 435/128, 129, 197, 876, 939

[56] References Cited

U.S. PATENT DOCUMENTS 4,859,796  8/1989  Hurtel et al. ............................ 564/204

FOREIGN PATENT DOCUMENTS 2 423 482  11/1979  France .
30 48 020   7/1982  Germany .
40 27 843   3/1992  Germany .
  788 079  12/1957  United Kingdom .

OTHER PUBLICATIONS

Susana Puertas et al, "Lipase Catalyzed Aminolysis of Ethyl Propiolate and Acrylic Esters. Synthesis of Chiral Acrylamides", 1993, Tetrahedron, vol. 49, No. 19, pp. 4007–4014.

Database WPI, Section Ch, Week 9329, Derwent Publications Ltd., London, GB; Class D16, AN 93–231503 XP002039451 & JP 05 153 986 A (Lion Corp), Jun. 22, 1993.

*Primary Examiner*—Shailendra Kumar
*Attorney, Agent, or Firm*—Oblon, Spivak, McClelland, Maier & Neustadt, P.C.

[57] ABSTRACT

A process for preparing acrylic or methacrylic acid amides functionalized with a cationizable tertiary amine, by aminolysis of acrylic or methacrylic acid esters with the aid of enzymes.

17 Claims, No Drawings

PROCESS FOR PREPARATION OF ACRYLIC OR METHACRYLIC ACID AMIDES

BACKGROUND OF THE INVENTION

1. Field of the Invention

This present invention relates to a process for preparing acrylic or methacrylic acid amides functionalized with cationizable tertiary amino groups by aminolysis of acrylic or methacrylic acid esters with the aid of enzymes. The present invention also relates to the acrylic or methacrylic acid amides obtained by this process.

2. Description of the Background

Many processes are known for obtaining acrylic amides from the corresponding esters by reaction with amines which prevent or minimize the secondary so-called Michael reaction resulting from the addition of the amine to the double acrylic or methacrylic bond. Thus, the patent FR 2,259,088 discloses a process in several stages going through the formation of an intermediate product such as β-amino-propionamide which is then treated thermally at high temperatures. However, this process has the drawback of generating undesirable decomposition products and of having a low overall yield.

Another known solution (FR 2,423,482) requires use of a dialkylated tin-oxide based catalyst as an accelerant for the aminolysis reaction. But such a process makes use of compounds which may not satisfy the current concerns regarding the environment.

In order to mitigate the various problems set forth above, another known method (FR 2,590,567) discloses a process of reacting an acrylic or methacrylic anhydride with a diamine. But this method has the disadvantage of requiring a costly anhydride which is difficult to obtain, and produces acrylic or methacrylic acid as a by-product.

SUMMARY OF THE INVENTION

Confronted with these various drawbacks, the inventors have developed a process which overcomes many of the problems discussed above.

It is an object of the present invention to provide a process for preparing acrylic or methacrylic acid amides functionalized with cationizable tertiary amino groups.

It is another object of the present invention to provide a process in which the yield of side-products resulting from the Michael reaction is minimized.

It is another object to provide a process for preparing acrylic or methacrylic acid amides functionalized by a cationizable tertiary amine with a high overall yield and a low rate of secondary reactions, such as polymerization or the Michael reaction, involving operating conditions and reactants which may comply with current environmental standards and/or regulations.

The objects of the present invention and others are accomplished by reacting an acrylic or methacrylic acid ester with a diamine in the presence of at least one polymerization inhibitor and at least one enzyme, to produce the corresponding acrylic or methacrylic acid amide, where the diamine has (1) an amino group capable of reacting with the ester group of the acrylic or methacrylic acid ester to form an amide group and (2) a cationizable tertiary amino group; and the active site of the enzyme recognizes the ester group of the acrylic or methacrylic acid ester.

Various other objects, features and attendant advantages of the present invention will be more fully appreciated as the same becomes better understood from the following detailed description.

DESCRIPTION OF THE PREFERRED EMBODIMENTS

The present invention provides a process for preparing acrylic or methacrylic acid amides functionalized with cationizable tertiary amino groups, which are useful for preparing polymers that contain cationizable tertiary amino groups. The starting material for the present process may be an acrylic or methacrylic acid ester. Any diamine may be used in the process which has an amino group capable of reacting with the ester group of the acrylic or methacrylic acid ester to form an amide group and a cationizable tertiary amino group. The amino functionality which forms the amide group may be primary or secondary. Primary amino groups are preferred. The term "cationizable tertiary amino group" refers to a trisubstituted amino group which can be protonated or quaternized with, for example, an alkylating agent.

The reaction of the acrylic or methacrylic acid ester and the diamine is conducted in the presence of an enzyme which has an active site that recognizes the ester group of the acrylic or methacrylic acid ester. Without being limited to any theory, the enzyme may interact with the ester group and thereby lowers the activation energy for reaction with the diamine to form the corresponding amide group. The interaction between the enzyme and the acrylic or methacrylic acid ester may reduce the amount of side-products produced via the Michael reaction, i.e., addition of the diamine to the double bond of the acrylic or methacrylic acid ester.

In a preferred embodiment, the amide product of the present process is an alkyl or oxyalkyl N-dialkylamino acrylamide or methacrylamide represented by formula (I):

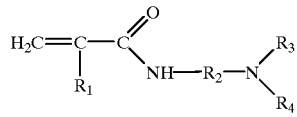

(I)

where
- $R_1$ is a hydrogen atom or a methyl radical;
- $R_2$ is a linear or branched alkyl radical having 1 to 20 carbon atoms or an oxyalkylated radical having 1 to 50 alkylene oxide radicals; and
- $R_3$ and $R_4$ are each, independently, a linear or branched alkyl radical having 1 to 18 carbon atoms.

As used herein, the term "branched alkyl radical" includes cyclic structures unless noted otherwise. $R_2$ may have 1 to 20 carbon atoms. This range includes all specific values and subranges therebetween, including 2, 5, 8, 10, 12, 14, and 18 carbon atoms. Alternatively, $R_2$ may be an oxyalkylated radical having 1 to 50 alkylene oxide radicals. The alkylene oxide units may be derived from, for example, ethylene oxide, propylene oxide, or a mixture thereof. $R_2$ may have 1 to 50 alkylene oxide units therein. This range includes all specific values and subranges therebetween, including 2, 5, 10, 15, 20, 25, 30, 35, 40, and 45 alkylene oxide units. $R_2$ should be selected such that the primary amino group is not sterically hindered to such a degree that this functionality is incapable of reacting with the ester group of the acrylate of methacrylate. Most preferably, $R_2$ has a structure such that the degree of steric hinderance at the primary amino group is minimal.

$R_3$ and $R_4$ may be the same or different. Each group may have 1 to 18 carbon atoms. This range includes all specific values and subranges therebetween, including 2, 5, 8, 10, 12, and 14 carbon atoms.

Amide (I) may be produced from an acrylic or methacrylic alkyl ester represented by the formula:

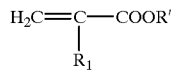

where
R₁ is defined above; and
R' is a linear or branched alkyl radical.
R' may have 1 to 20 carbon atoms. Preferably, R' has 1 to 15 carbon atoms, more preferably 1 to 10 carbon atoms, even and more preferably 1 to 5 carbon atoms. Most preferably, R' is a methyl or ethyl radical. Particularly preferred acrylic and methacrylic esters include, for example, methyl acrylate, ethyl acrylate, methyl methacrylate, and ethyl methacrylate.

The diamine is preferably represented by the of the formula:

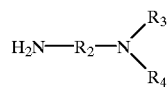

where $R_2$, $R_3$ and $R_4$ are defined above.

The reaction between the acrylic or methacrylic ester and the diamine is conducted in the presence of at least one polymerization inhibitor. The polymerization inhibitor may be chosen from among any of the polymerization inhibitors well-known to the individual skilled in the art. Preferable polymerization inhibitors include, for example alloocimene, hydroquinone, hydroquinone methyl ether, phenothiazine, and 2,6-terbutyl-p-cresol. Mixtures of polymerization inhibitors may be used.

Among these enzymes for use in the present invention, the lipases of various origins such as, for example, fungal or bacterial or even animal origin, are preferred. Among the lipases of bacterial or fungal origin, the lipases of *Chromobacterium viscosum, Aspergillus niger, Mucor miehei, Rhizopus arrhizus, Candida cylindracea, Candida antarctica, Rhizopus delemar, Mucor javanicus, Pseudomonas fluorescens* may be used. As a lipase of animal origin, hog-pancreas lipase is suitable.

More preferably, the enzyme is immobilized on a solid support. Even more preferably, the enzyme or enzymes used in the process according to the invention are chosen from among a *Candida antarctica* lipase immobilized on a macroporous acrylic-type resin known under the name Novozyme® or else a *Mucor miehei* lipase known under the name Lipozyme®, or a mixture thereof.

The activity of the enzyme may vary over a wide range. The activity of the lipase is preferably at least 3000 propyl laurate units (PLU)/g, more preferably at least 5000 PLU/g and, most preferably at least 6500 PLU/g. The lipase may also have an activity of at least 20 batch interesterification units (BIU)/g, more preferably at least 30 BIU/g and, most preferably, at least 40 BIU/g. Propyl laurate units may be determined using a batch ester synthesis assay where, as substrates, 1-propanol and lauric acid are reacted at 60° C. for 15 minutes in the presence of the enzyme. A detailed description of this assay is available from Novo Nordisk in the product information for NOVOZYM 435. Batch interesterification units may be determined using a batch acidolysis assay where, as substrates, high oleic sunflower oil and decanoic acid are reacted at 70° C. for 60 minutes in the presence of the enzyme. A detailed description of this assay is available from Novo Nordisk in the product information for LIPOZYME IM.

The amount of enzyme in the reaction is not particularly limited, and may vary over a wide range. The amount of enzyme used in the present process may be 1 to 25% by weight, based on the amount of acrylic or methacrylic ester. More preferably, this amount is 2 to 20% by weight, and, most preferably 5 to 15% by weight, based on the amount of acrylic or methacrylic ester. These ranges include all specific values and subranges therebetween, including 2, 4, 8, 10, 12, and 18% by weight.

The reaction according to the invention is preferably carried out at atmospheric pressure and at a temperature ranging of 20° C. to 100° C. More preferably, the reaction temperature is 40° C. to 90° C. These temperature ranges include all specific values and subranges therebetween, including 25, 30, 35, 45, 50, 60, 70, 80, and 85° C.

The reaction time may vary over a wide range. The reaction may be conducted for any convenient length of time, such as, for example, 2 to 48 hours. This range includes all specific values and subranges therebetween, including 3, 4, 5, 10, 15, 20, 25, 30, 35, and 40 hours.

In a particularly, preferred embodiment of the present invention, air is bubbled through the reaction mixture. Without being limited to any theory, the air may remove the alcohol by-product of the reaction and thereby drive the reaction towards the desired amide product. The air may also inhibit polymerization of the vinyl groups. The flow rate of air through the reaction medium may vary with the size of the reactor used. The flow rate may be 0.1 to 250 liters/hr, inclusive of all specific values and subranges therebetween.

The gross reaction product obtained after cooling the reaction mixture may contain the alkyl or oxyalkyl N-dialkylamino acrylamide or methacrylamide of formula (I) corresponding to the original ester, the excess diamine and/or ester not having reacted, the products of the Michael reaction as well as the enzyme or enzymes used in the course of the reaction. The enzymes may be recovered by filtration. The composition of the gross product obtained may be determined qualitatively and quantitiatively by RMN ¹H analysis of the gross product in solution in deuterated chloroform.

A preferred embodiment of the invention is an aminolysis reaction of methyl methacrylate with 3-dimethylaminopropylamine in the presence of lipases of the Novozyme® or Lipozyme® type in order to obtain 3-dimethylamino-propylmethacrylamide.

The yield of the amide product of the present process is preferably at least 50%, based on the amount of the acrylic or methacrylic ester. More preferably, the yield is at least 75%, and, even more preferably, at least 85%. Most preferably, the yield is at least 90%. The yield may be even higher, e.g., up to 100% conversion.

The yield of the undesired Michael addition products is preferably at most 20%, based on the amount of the acrylic or methacrylic ester. More preferably, the yield of Michael reaction products is at most 15% and, most preferably, at most 10%. The yield of Michael reaction products may be lower than 10%, e.g., at most 8, 6, 4 or 2%.

The ratio of the desired amide product to the undesired Michael addition product is preferably at least 2:1, more preferably at least 5:1, even more preferably at least 10:1, and, most preferably, at least 20:1. This ratio may be even higher, such as at least 25:1, 30:1, 40:1, 50:1, or 99:1.

Having generally described this invention, a further understanding can be obtained by reference to certain specific examples which are provided herein for purposes of illustration only and are not intended to be limiting unless otherwise specified.

EXAMPLES

Example 1

901.6 g of methyl methacrylate, 0.9 g of alloocimene and 80.1 g of *Candida antarctica* lipase marketed by the Novobioindustrie company under the name of Novozyme® with activity of 7400 PLU/g (PLU=Propyl Laurate Units) were fed under agitation and at room temperature into a one-liter reactor equipped with a mechanical agitation system, a cooler and an oil-bath heating system.

After a rise in temperature to 60° C., 119.4 g of 3-dimethylamino-propylamine were added in continuous manner for 9 hours with the aid of a stainless-steel submerging rod and under bubbling air having a flow of 180 liters/hour as well as 988.7 g of methyl methacrylate corresponding to the methyl methacrylate mass borne along by the bubbling. It should be noted that the air bubbling alters the balance through bearing along of the methanol formed by the aminolysis reaction and prevents polymerization of the monomers. At the end of the injection period, the heating was shut off and the agitation maintained for one hour.

The product then obtained was cooled at room temperature, then filtered. The filtrate was a solution consisting of methyl methacrylate, amine which has not reacted, formed methacrylamide, as well as products of the Michael reaction. The yields were determined with respect to the amine involved with the aid of analysis of RMN $^1$H spectra performed on filtrate solutions in deuterated chloroform. Accordingly, for this test the filtrate contained 97% 3-dimethylamino-propylmethacrylamide and 3% Michael products, thus resulting in a high conversion to amide (97%) and a low formation of Michael products (3%).

Example 2

903.4 g of methyl methacrylate, 1.1 g of alloocimene, 80 g of the same lipase as that used in the preceding Example were introduced at room temperature into a reactor identical to the one described in the preceding Example.

After a rise in the temperature to 60° C., 127.3 g of the same diamine as that described in Example 1 were added in continuous manner for 15 hours with the aid of a stainless-steel submerging rod, under bubbling air implemented with the aid of a gas diffuser, at a flow of approximately 50 liters/hour. 82 g of methyl methacrylate corresponding to the methyl methacrylate mass borne along by said bubbling were added at the time of the reaction in order to keep the reaction volume constant. At the end of the injection period, the heating was shut off and the agitation maintained for one hour. The product obtained then was cooled at room temperature, then filtered.

The filtrate was a 90% solution of 3-dimethylaminopropylmethacrylarnide determined with the aid of analysis of RMN $^1$H spectra performed on the filtrate in solution in deuterated chloroform, thus showing that it is possible to decrease the flows of air and amine while preserving a high rate of conversion to amide (90%) and a low content of Michael products (10%).

Example 3

In this Example, the same compounds as those used in Example 1 were caused to react in the presence of half the quantity of Novozyme® with respect to the amine.

Thus, 450 g of methyl methacrylate, 0.45 g of alloocimene and 40.1 g of *Candida antarctica* lipase marketed by the Novobioindustrie company under the name of Novozyme® with activity of 7400 PLU/g (PLU=Propyl Laurate Units) were introduced, under agitation and at room temperature, into an apparatus identical to the one described in Example 1.

After a rise in the temperature to 60° C., 123.6 g of 3-dimethylaminopropylamine were added in continuous manner for 18 hours with the aid of a stainless-steel submerging rod and under bubbling air having a flow of 180 liters/hour as well as 555.5 g of methyl methacrylate corresponding to the methyl methacrylate mass borne along by said bubbling.

It should be noted that the air bubbling alters the balance by bearing along of the methanol formed at the time of the aminolysis reaction and prevents polymerization of the monomers. At the end of the injection period, the heating was shut off and agitation maintained for one hour.

The filtrate contained 92% dimethylaminopropyl methacrylamide, 6% Michael products and 2% residual amine, a composition determined with the aid of analysis of RMN $^1$H spectra performed on the filtrate in solution in deuterated chloroform, thus yielding a high conversion to amide (92%) and a low formation of Michael products (6%).

Example 4

In this Example, the ester aminolysis reaction was conducted at 40° C.

Thus 900.7 g of methyl methacrylate, 0.9 g of alloocimene and 80.1 g of *Candida antarctica* lipase marketed by the Novobioindustrie company under the name of Novozyme® with an activity of 7400 PLU/g (PLU=Propyl Laurate Units) were introduced, under agitation and at room temperature, into an apparatus identical to that described in Example 1.

After a rise in temperature to 40° C., 123.6 g of 3-dimethylaminopropylamine were added in continuous manner for 9 hours with the aid of a stainless-steel submerging rod under bubbling air having a flow of 180 liters/hour, as well as 555.5 g of methyl methacrylate corresponding to the methyl methacrylate mass borne along by the bubbling.

It should be noted that the bubbling air alters the balance by bearing along of the methanol formed at the time of the aminolysis reaction and prevents polymerization of the monomers.

At the end of the injection period, the heating was shut off and the agitation maintained for one hour.

The composition of the filtrate, determined with the aid of analysis of the RMN $^1$H spectra performed on the filtrate in solution in deuterated chloroform, was: 79% 3-dimethylaminopropylmethacrylamide, 17% Michael products and 4% residual amine, thus yielding a high conversion to amide (79%) with a formation of Michael products on the order of 17%.

Example 5

In this Example, the ester aminolysis reaction was conducted at 90° C.

Using quantities of reagents identical to those in the preceding Example, as well as with an operating method similar to that described in the preceding Example, with the exception of the reaction temperature which was 90° C., there was obtained a filtrate the composition of which, determined with the aid of analysis of the RMN $^1$H spectra performed on the filtrate in solution in deuterated chloroform, was 96% 3-dimethylaminopropylmethacrylamide and 4% Michael products, thus resulting in a high conversion to amide (96%) and a low formation of Michael products (4%).

Example 6

47.2 g of methyl methacrylate, 0.059 g of monomethylether hydroquinone and 9 g of *Mucor miehei* lipase marketed by the Novobioindustrie company under the name of Lipozyme® with activity of 7.7 BAUN/g (BAUN=Batch Acidolysis Uriit Novo) or with activity of 45/BIU/g (BIU=Batch Interesterification Units) were fed under agitation and at room temperature into a 0.2-liter double-walled reactor equipped with a magnetic agitation system and an oil-circulation heating system.

After a rise in temperature to 40° C., 7.3 g of 3-dimethylaminopropylamine were added in continuous manner for 6 hours with the aid of a bromine flask and under bubbling air having a flow of 180 liters/hour as well as 8.5 g of methyl methacrylate corresponding to the methyl methacrylate mass borne along by the bubbling.

At the end of the injection period, the heating was shut off and the agitation maintained for thirty minutes.

The product then obtained was cooled at room temperature, then filtered. The filtrate was a solution consisting of methyl methacrylate, amine not having reacted, formed methacrylamide, as well as products of the Michael reaction.

Yield calculations are determined with the aid of analysis of the RMN $^1$H spectra performed on the filtrate in solution in deuterated chloroform.

Accordingly, for this test the filtrate contained 83% 3-dimethylaminopropylmethacrylamide, 16% Michael products and 1% residual amine, thus resulting in a high conversion to amide (83%).

Example 7

In this Example, 901 g of methyl acrylate, 0.9 g of alloocimene, 80 g of lipase marketed under the name of Novozyme® with activity of 7400 PLU/g and 119 g of 3-dimethylaminopropylamine were caused to react with the same operating method and the same equipment as those described in Example 1.

The product contained 97% 3-dimethylaminopropylacrylamide and 3% Michael products determined with the aid of analysis of RMN $^1$H spectra performed on the filtrate in solution in deuterated chloroform.

Example 8

In this Example, Example 1 was reproduced.

As in Example 1, a filtrate with a composition identical to that of Example 1 was obtained. The enzyme used in this reaction was then completely recovered, and then reused in an operation identical in every way to the preceding reaction.

The filtrate obtained contained 96% 3-dimethylaminopropylmethacrylamide and 4% Michael products determined with the aid of analysis of RMN $^1$H spectra performed on the filtrate in solution in the deuterated chloroform.

Another complete recovery of the enzyme and another use under the same conditions as before afforded a product having a composition of 94% 3-dimethylaminopropylmethacrylamide and 6% Michael products, determined with the aid of analysis of RMN $^1$H spectra performed on the filtrate in solution in deuterated chloroform.

This demonstrated that it is possible to use the same enzyme sample at least 3 times, with a yield always in excess of or equal to 94%.

This application is based on French Patent Application No. 96-15612, incorporated herein by reference in its entirety.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing acrylic or methacrylic acid amides functionalized with cationizable tertiary amino groups, comprising:

reacting an acrylic or methacrylic acid ester with a diamine in the presence of at least one polymerization inhibitor and at least one enzyme, to produce an acrylic or methacrylic acid amide, wherein the diamine has (1) an amino group capable of reacting with the ester group of the acrylic or methacrylic acid ester to form an amide group and (2) a cationizable tertiary amino group; and the active site of enzyme recognizes the ester group of the acrylic or methacrylic acid ester.

2. The process of claim 1, wherein the acrylic or methacrylic acid ester is represented by the formula:

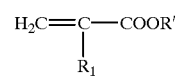

the diamine is represented by the formula:

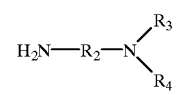

and the amide functionalized with a cationizable tertiary amino group is represented by formula (I):

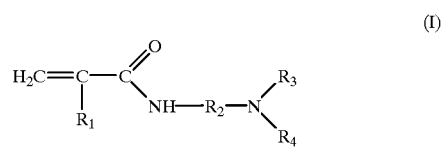

wherein $R_1$ is a hydrogen atom or a methyl radical;

R' is a linear or branched alkyl radical;

$R_2$ is a linear or branched alkyl radical having 1 to 20 carbon atoms or an oxyalkylated radical containing 1 to 50 alkylene oxide radicals; and $R_3$ and $R_4$ are each, independently, a linear or branched alkyl radical having 1 to 18 carbon atoms.

3. The process of claim 2, wherein R' is a methyl or ethyl radical.

4. The process of claim 2, wherein the alkylene oxide radicals are ethylene and/or propylene oxide radicals.

5. The process of claim 2, wherein $R_1$ and R' are each a methyl radical and the diamine is 3-dimethylaminopropylamine.

6. The process of claim 1, wherein the enzyme is a lipase of fungal, bacterial or animal origin.

7. The process of claim 6, wherein the lipase is derived from *Chromobacterium viscosum, Aspergillus niger, Mucor miehei, Rhizopus arrhizus, Candida cylindracea, Candida antarctica, Rhizopus delemar, Mucor javanicus, Pseudomonas fluorescens* or a hog-pancreas lipase.

8. The process of claim 7, wherein a mixture of two or more of the lipases are used.

9. The process of claim 7, wherein the lipase is a *Candida antarctica* lipase, *Mucor miehei* lipase, or a mixture thereof.

10. The process of claim 1, wherein the reaction temperature is 20° C. to 100° C.

11. The process of claim 1, wherein the reaction temperature is 40° C. to 90° C.

12. The process of claim 1, wherein the enzyme is immobilized on a solid support.

13. A process for preparing an acrylic or methacrylic acid amide represented by formula (I):

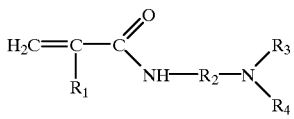
(I)

comprising:

reacting an acrylic or methacrylic acid ester represented by the formula:

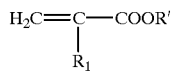

with a diamine represented by the formula:

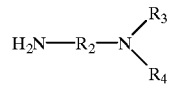

in the presence of at least one polymerization inhibitor and a lipase which has an active site that recognizes the ester group of said acrylic or methacrylic acid ester, to produce said amide, wherein $R_1$ is a hydrogen atom or a methyl radical;

R' is a linear or branched alkyl radical;

$R_2$ is a linear or branched alkyl radical having 1 to 20 carbon atoms or an oxyalkylated radical containing 1 to 50 alkylene oxide radicals; and $R_3$ and $R_4$ are each, independently, a linear or branched alkyl radical having 1 to 18 carbon atoms.

14. The process of claim 13, wherein R' has 1 to 20 carbon atoms.

15. The process of claim 14, wherein R' is a methyl or ethyl radical.

16. The process of claim 15, wherein $R_2$ is a linear or branched alkyl radical having 1 to 20 carbon atoms.

17. The process of claim 16, wherein $R_3$ and $R_4$ are each a methyl radical.

* * * * *

UNITED STATES PATENT AND TRADEMARK OFFICE
CERTIFICATE OF CORRECTION

PATENT NO. : 5,973,203

DATED : October 26, 1999

INVENTOR(S): Jean-Bernard Egraz, et al.

It is certified that an error appears in the above-identified patent and that said Letters Patent is hereby corrected as shown below:

COLUMN 3, LINE 19
"The diamine is preferably represented by the of the formula:"
should read,
--The diamine is preferably represented by the formula:--

Signed and Sealed this

Seventeenth Day of April, 2001

*Attest:*

NICHOLAS P. GODICI

*Attesting Officer*  *Acting Director of the United States Patent and Trademark Office*